United States Patent [19]

Buchanan et al.

[11] Patent Number: 5,265,609

[45] Date of Patent: Nov. 30, 1993

[54] NONMAGNETIC BODY MOVEMENT DETECTOR AND BIOMAGNETOMETER UTILIZING THE DETECTOR

[75] Inventors: D. Scott Buchanan, Escondido; Scott Riley, Oceanside, both of Calif.

[73] Assignee: Biomagnetic Technologies, Inc., San Diego, Calif.

[21] Appl. No.: 751,178

[22] Filed: Aug. 28, 1991

[51] Int. Cl.$^5$ ................................ A61B 5/05
[52] U.S. Cl. ................................ 128/653.1; 324/248; 128/782
[58] Field of Search ............... 128/653.1, 653.2, 653.5, 128/782; 324/244, 248, 244.1, 260, 262

[56] References Cited

U.S. PATENT DOCUMENTS

| | | | |
|---|---|---|---|
| 3,629,594 | 12/1971 | Sandberg | 128/782 |
| 3,861,807 | 1/1975 | Lescrenier | |
| 4,793,355 | 12/1988 | Crum et al. | 128/653.1 |
| 4,945,916 | 8/1990 | Kretchmer et al. | 128/782 |
| 4,972,836 | 11/1990 | Schenck et al. | 128/653.2 |
| 5,103,823 | 4/1992 | Acharya et al. | 128/653.1 |

FOREIGN PATENT DOCUMENTS

| | | |
|---|---|---|
| 0359864 | 3/1990 | European Pat. Off. ......... 128/653.1 |
| 3216273 | 11/1983 | Fed. Rep. of Germany ... 128/653.1 |
| 2137159 | 12/1972 | France . |
| 2489137 | 3/1982 | France . |

Primary Examiner—Lee S. Cohen
Assistant Examiner—K. M. Pfaffle
Attorney, Agent, or Firm—Gregory Garmong

[57] ABSTRACT

An apparatus for making magnetic measurements of the human body includes a biomagnetometer having a magnetic field sensing coil that measures magnetic fields arising from a selected portion of a body. A position monitor used in conjunction with the biomagnetometer produces no magnetic fields that can interfere with the taking of magnetic field measurements, and can operate simultaneously with the taking of magnetic field measurements. The position monitor includes an optical target mounted on the selected portion of the body, the optical target having a variation in light reflectance across the target. An input optical guide directs a beam of light at the target, an output optical guide collects a reflected beam of light from the target, and a limit detector receives the beam of light from the output optical guide and determines whether the intensity of the received light varies outside of predetermined limits.

16 Claims, 2 Drawing Sheets

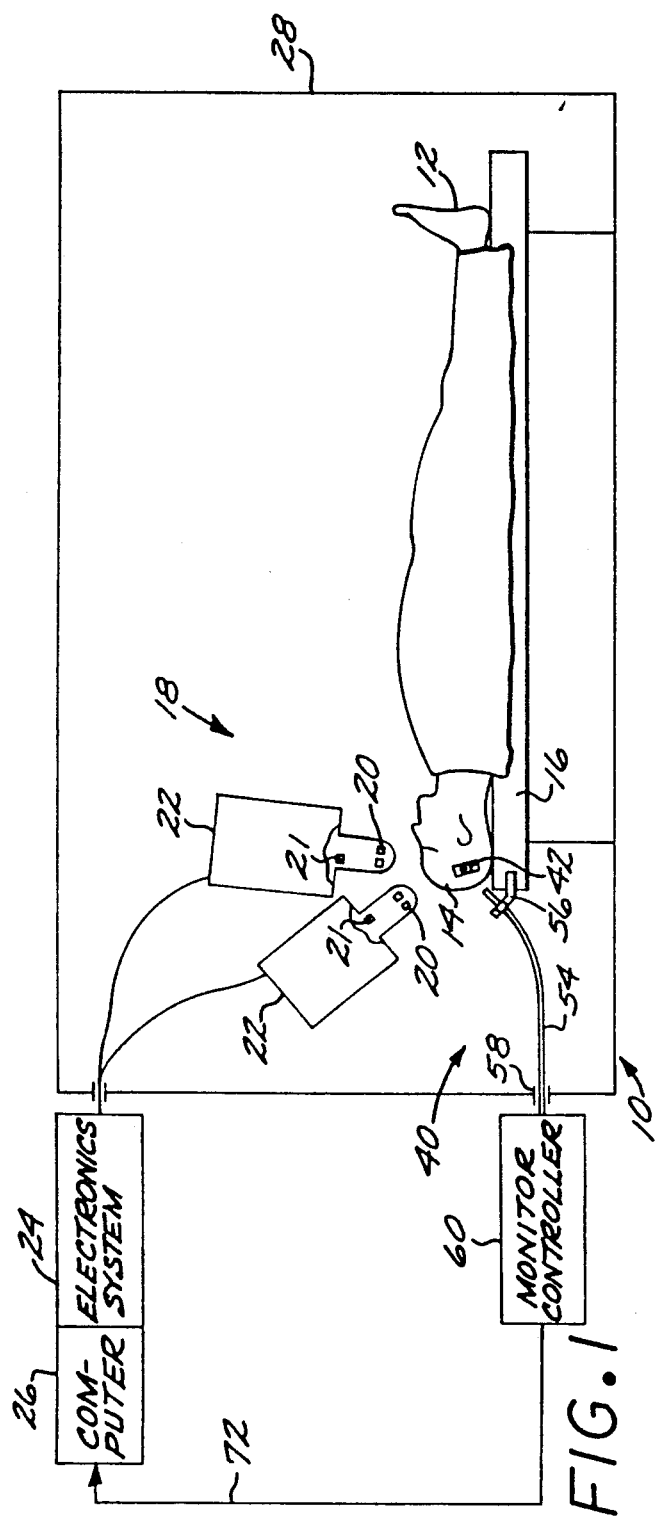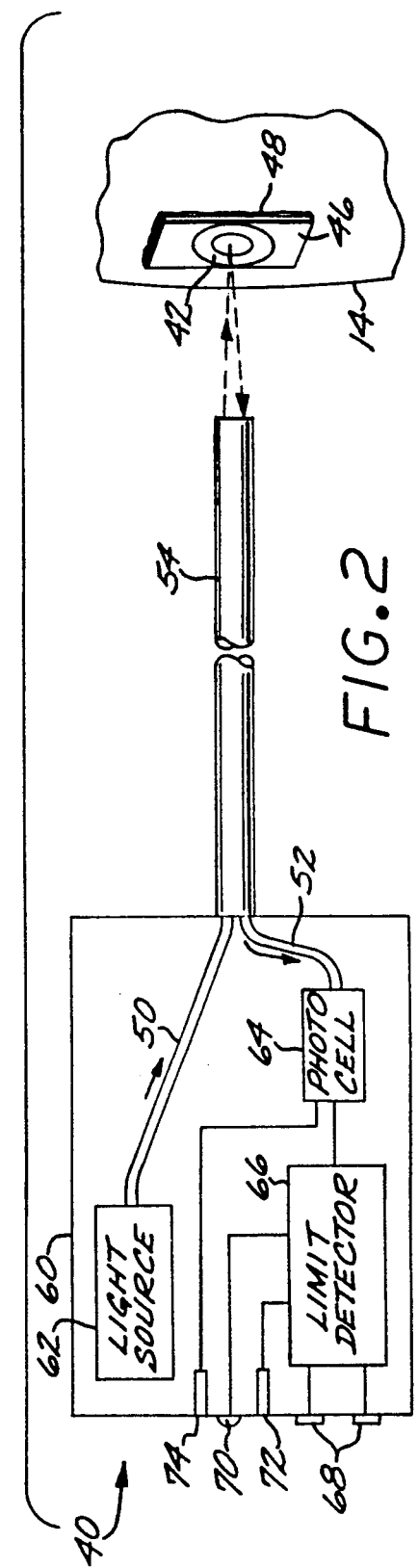

NONMAGNETIC BODY MOVEMENT DETECTOR AND BIOMAGNETOMETER UTILIZING THE DETECTOR

BACKGROUND OF THE INVENTION

This invention relates to the measurement of small magnetic fields produced by the body, and, more particularly, to the measurement of the position of the body as the magnetic field measurements are taken.

The biomagnetometer is a device that measures the very small magnetic fields produced by the human body. The magnetic fields, particularly those produced by the brain and the heart, can be important indicators of the health of the body, because aberrations in the magnetic field can be associated with certain types of disfunctions either for diagnosis or early prediction. Moreover, the magnetic fields produced by the brain are an indicator of thought processes and where such processes occur, and can be used to investigate the mechanisms of thought.

Magnetic fields produced by the body are very small. Typically, the strength of the magnetic field produced by the brain is about 0.00000001 Gauss. By comparison, the strength of the earth's magnetic field is about 0.5 Gauss, or over ten million times larger than the magnetic field of the brain.

The biomagnetometer must therefore include a very sensitive detector of magnetic fields. Current biomagnetometers utilize a pickup coil which produces an electrical current when a magnetic field penetrates the pickup coil. The electrical current, which is typically very small in magnitude, is detected by a Superconducting QUantum Interference Device, also known by the acronym SQUID. Spurious effects from the detection of other magnetic fields than those produced by the brain can be removed by appropriate filters. However, the ability of filters to remove all of the extraneous effects is limited. To further improve the signal-to-noise ratio of the system, the subject and pickup coil can be located in a magnetically shielded room. The operation of SQUIDs and their electronics are disclosed in U.S. Pat. Nos. 3,980,076; 4,079,730; 4,386,361; and 4,403,189. A magnetically shielded room is disclosed in U.S. Pat. No. 3,557,777. The disclosures of all of these patents are incorporated herein by reference.

Ultimately, of course, the results of biomagnetic measurements are of most value if they can be associated with their location of origin within the body. To make this association, there are two steps required. The location of origin in space of the magnetic field signal must be determined, and then this location in space must be associated with the position of the body that produces the signal. The location of origin in space can be determined by various modeling, measurement, or analytical techniques. One such approach is the lead field synthesis methodology of U.S. Pat. No. 4,977,896, whose disclosure is incorporated by reference.

The location of the body in space, and thence relative to the location of origin of the magnetic field, was for some period of time accomplished by constraining the subject to a known location. For example, if brain signals were being measured, the head of the subject was held in a known fixed position with head restraints. However, restraints may be uncomfortable and also can result in interfering brain signals as the attention of the subject is focused upon the restraints. An important step forward was made with the discovery of an electromagnetic position sensing device, which is described in U.S. Pat. No. 4,793,355, whose disclosure is incorporated by reference.

The electromagnetic position sensing device utilizes electromagnetic transmitters and receivers to determine the position of the subject's body. For example, a transmitter can be located at a fixed location relative to the sensing coil, and a number of receivers can be fixed to the head of the subject. The signal received by the receivers is analyzed to determine the head position of the subject.

Because the electromagnetic position sensing device itself can generate magnetic fields that are detected by the biomagnetic sensing coil, in some applications the position sensing system is operated intermittently with the taking of biomagnetic data. That is, the electromagnetic position sensing system is operated to determine the head position and turned off. The biomagnetometer is operated to take brain signal data for a period of time and turned off. The two systems continue operating in this intermittent fashion to take data on both head position and magnetic fields produced from the head of the subject. (For more detail, see col. 5, lines 17-30 and col. 13, lines 4-27 of U.S. Pat. No. 4,793,355.)

This intermittent operation approach is completely satisfactory for many situations. However, in others it may be necessary to continue the taking of biomagnetic data for long periods of time, during which the position of the subject may shift. That shift in position may make it impossible to make the association between head position and magnetic field signal. One solution to the problem is to operate the electromagnetic position sensing system continuously at a frequency that is not of interest in the biomagnetic field studies, as described at col. 5, lines 31-38 and col. 13, lines 28-35 of U.S. Pat. No. 4,793,355.

However, there remain some situations where neither of these approaches is fully satisfactory. There therefore exists a need for another approach for determining the position and movement of the body of the subject simultaneously with the taking of biomagnetic field measurements. Such an approach should not interfere with the taking of biomagnetic field data, and should not be obtrusive to the subject so that it would generate spurious brain signals. The present invention fulfills this need, and further provides related advantages.

SUMMARY OF THE INVENTION

The present invention provides an apparatus for making biomagnetic field measurements and for simultaneously and automatically determining the position and movement of the portion of the body from which the signal originates. The position monitor is fully compatible with existing and planned biomagnetometers. It is not obtrusive to the subject, and is readily integrated with typical measurement protocols. The position monitor is also relatively low in complexity and inexpensive.

In accordance with the invention, apparatus for making magnetic measurements of the human body comprises biomagnetometer means including a magnetic field sensing coil for measuring magnetic fields arising from a selected portion of a body; and means for simultaneously determining movement of the selected portion of the body of more than a predetermined amount, the means for automatically determining itself creating no magnetic field that may be detected by the biomagnetometer means.

The means for automatically determining movement is preferably embodied in a position monitor that directs a signal against a target on the selected portion of the body and receives a signal back from the target on the selected portion of the body, wherein the position monitor itself creates no magnetic field that may be detected by the biomagnetometer means. Most preferably, the position monitor includes an optical target mounted on the selected portion of the body, the optical target having a variation in light reflectance thereon, an input optical guide that directs a beam of light at the target, an output optical guide that collects a reflected beam of light from the target, and a limit detector that receives the beam of light from the output optical guide and determines whether the intensity of the received light varies outside of predetermined limits. The input and output optical guides are conveniently formed as optical fiber bundles. The input and output optical fiber guides may be packaged within a single optical guide housing for convenience. In operation of the position monitor, if the selected part of the body moves, the reflectance of the target changes. The reflectance thus becomes a measure of the position of the body.

A light beam does not generate a magnetic field that is detected by the magnetic field sensing coil. The optical guides are stationary, and produce no field. The limit detector typically operates by detecting the intensity of the light signal, converting that intensity to an electrical signal, and performing limit detection measurements of the electrical signal. The converted electrical signal has the potential of being detected by the magnetic field sensing coil, but it can be effectively shielded or placed at a sufficient distance from the magnetic field sensing coil that any potential interference is sufficiently attenuated. Thus, the present approach is fully "nonmagnetic" in the sense that it does not interfere with the taking of biomagnetic data.

The present technique is also readily used and not obtrusive to the subject. The only portion of the system contacting the subject is the target. The target is desirably fixed to a paper or other light weight support which can be adhesively attached to the body and then easily removed when the measurements are complete. The optical guide housing with the optical guides therein is positioned adjacent the body of the subject so that the light beam is directed at the target, but the optical guides and housing do not touch the subject and may not even be known to the subject. Other features and advantages of the invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 1 is a side elevational view of an apparatus in accordance with the invention, with a subject in position for measurement;

FIG. 2 is a schematic view of the position monitor;

DETAILED DESCRIPTION OF THE PREFERRED EMBODIMENT

Figure 3:
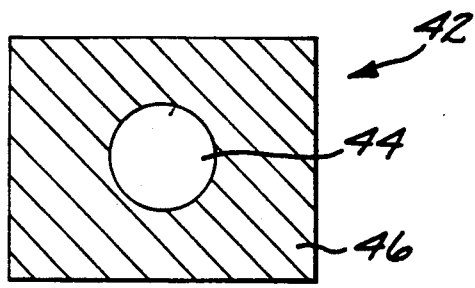
FIG. 3 is an elevational view of the target.
Figure 4:
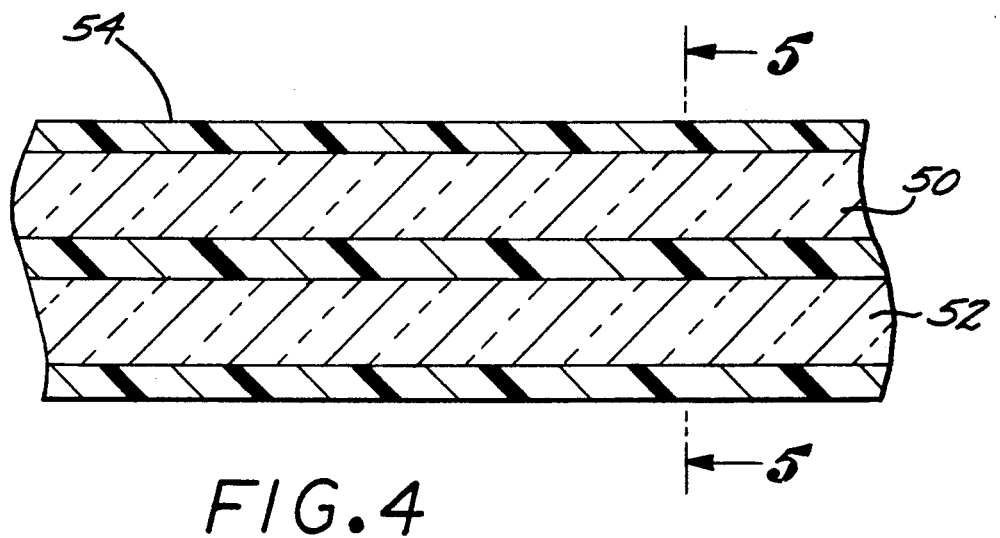
FIG. 4 is a side sectional view of the optical guide housing.
Figure 5:
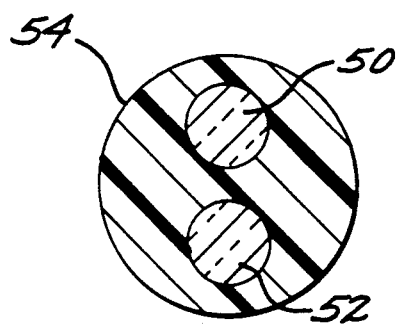
FIG. 5 is a cross sectional view of the optical guide housing.

As illustrated in FIG. 1, the present invention is preferably embodied in an apparatus 10 for obtaining biomagnetic data from the body 12 of a human patient or subject. More specifically, the data is normally obtained from biomagnetic sources within the head 14 of the person. The body 12 is placed upon a table 16 in proximity with a biomagnetometer 18. The biomagnetometer 18 includes a plurality of magnetic field sensing coils 20 for measuring small magnetic fields. The output signal of each magnetic field sensing coil 20 is detected by a detector, preferably a superconducting quantum interference device 21 (SQUID). Both the magnetic field sensing coil 20 and the SQUID 21 are maintained at a cryogenic operating temperature within a liquid helium dewar 22. In one preferred practice, and as illustrated, two dewars 22 are used, with 7 sensing coils and SQUIDs in each dewar. In another preferred practice, only one dewar 22 is used, with 37 sensing coils and SQUIDS in that dewar. This apparatus 10 gives good spatial resolution of the biomagnetic signals for reconstruction of their origin in space. The present invention is not so limited, however, and may be used in conjunction with biomagnetometers having more dewars 22, and larger or smaller numbers of sensing coils 20 and SQUIDS 21.

The magnetic signals from the brain are picked up by the magnetic field sensing coils 20 in the dewars 22, and the signals are detected by the SQUIDs 21. The SQUIDs 21 detect the magnetic field values as electrical currents that are processed in an electronics system 24 and stored in a computer 26 as a function of time. The sensors 20 and the body 12 of the patient are preferably, but not necessarily, enclosed within an enclosure 28 (also termed a magnetically shielded room or MSR) that shields the apparatus and magnetic field source from external magnetic influences. By screening off the external influences, the amount of signal processing and filtering required to obtain a meaningful indication of the biomagnetic field is reduced.

The position of the head 14 can be determined by the approach disclosed in U.S. Pat. No. 4,793,355. Alternatively, or additionally, the position of the head 14 can be monitored by a position monitor 40 whose relation to the head 14 is shown in FIG. 1 but which is shown in greater detail in FIG. 2.

The position monitor 40 includes a target 42 having a variation in reflectivity thereon. In the type of target 42 shown in FIG. 2 and FIG. 3, there is a central region 44 in the form of a circle of limited diameter within a background region 46. The central region 44 has one reflectivity for light, preferably a high reflectivity, and the background region 46 has another reflectivity, preferably a lower reflectivity. The central region may be divided into regions of varying reflectivity, if desired, for more spatial resolution. In a variation that may be useful in certain situations, the central region may have the lower reflectivity and the background region the higher reflectivity. The target 42 is fixed to the head 14 or other part of the body by mounting it on a support surface 46 that has a layer of medical adhesive 48 on the reverse side. The layer of adhesive 48 is normally protected by peel sheet (not shown), which is peeled away when the target is to be used. After use, the support surface and its target are discarded, or may be used again if desired.

An input optical guide 50 directs a beam of light at the central region 44 of the target 42. A portion of the light reflected from the central region 44 is collected by an output optical guide 52. The reflected beam is typically sufficiently well collimated that no additional lens is required, but one may be used if necessary. The input optical guide 50 and the output optical guide 52 are preferably optical fibers or optical fiber bundles. The guides 50 and 52 are preferably packaged together within an optical guide housing 54.

The optical guide housing 54 with its optical fiber guides 50 and 52 constitute a flexible cable. The optical guide housing is positioned by a clamp 56 from the table 16 as shown, a separate stand (not shown), or other fixed support. The optical guide housing 54 is positioned so that the light emitted from the input optical guide 50 is directed against the central region 44 of the target 52. The reflected light is collected by the output optical guide 52. If the reflected light intensity deviates downwardly more than some predetermined amount, it may be concluded that the target 42 has been moved relative to the output optical guide 52. This movement may be sideways, up or down, or tilted due to the movement of the head 14. The spacing between the input optical guide 50 and the output optical guide 52 determines the sensitivity of the position monitor 40 to changes in the spacing between the target 42 and the guides 50, 52.

The optical cable 54 passes through the wall of the enclosure 28 using a conventional shielded feed through 58. The remaining components of the position monitor 40, packaged in a monitor controller 60, are preferably located external to the enclosure 28.

The light that passes through the input optical guide 52 is provided from a light source 62. The light source 62 is preferably a pulse modulated red light emitting diode.

The reflected light collected by the output optical guide 52 is provided to a photocell 64, which produces an output signal related to the intensity of the light. The electrical output signal of the photocell is provided to a limit detector 66. The limits of the limit detector 66 are set by external controls 68. When the light intensity is within predetermined limits set through the controls 68, there is no output signal. When the light intensity falls outside those limits, there can be an audible or visual alarm output 70.

The limit detector 66 can also be used to provide an analog or digital output signal 72 to the computer 26. The output of the photocell 64 can also be made available as an analog output signal 74 for use by the computer 26 or otherwise.

A satisfactory optical fiber system, including the optical guides 50 and 52, housing 54, controller 60, light source 62, limit detector 66, and limit detector controls 68 can be purchased commercially as a single unit. An acceptable fiber-optic sensor system is the Model E3S-X3 available from Omron Corp.

Whether or not there is an electromagnetic position sensor of the type described in the '355 patent, the position monitor 40 of the present invention provides a simultaneous and automatic indication of whether the portion of the body under study has moved by more than the amount permitted by the settings of the limit detector. If the body part under study is moved in any manner that causes the reflected light to deviate by more than the permitted amount, there is a signal from the limit detector. This signal can be used in any of several ways in relation to the taking of biomagnetic data. In an essentially passive mode, the signal can be simply recorded with the biomagnetic data as a marker that certain data was obtained when the body had shifted. When the body is returned to the acceptable position such that the reflected light is within the limits set by the limit detector, an end condition can be indicated on the data. In a more active use of the position monitor, the operator can inform the subject that there has been an unacceptable movement. The subject can then readjust his or her position to return the reflectance to an acceptable level. Another possibility is to discontinue taking biomagnetic data until the position has been restored.

In these and other possible uses of the position monitor of the invention, an important advantage is that the position is being monitored continuously and simultaneously with the taking of biomagnetic data. If, for example, data collection for a particular study requires 20 minutes, during which the electromagnetic position sensing system must be continuously off, the present position monitor provides the only automatic indication of subject movement during that data-collection period.

Although a particular embodiment of the invention has been described in detail for purposes of illustration, various modifications may be made without departing from the spirit and scope of the invention. Accordingly, the invention is not to be limited except as by the appended claims.

What is claimed is:

1. Apparatus for making magnetic measurements of a human body, comprising:
   biomagnetometer means including a magnetic field sensing coil for measuring magnetic fields arising from a selected portion of the human body; and
   means for simultaneously determining movement of the selected portion of the human body of more than a predetermined amount, the means for simultaneously determining itself creating no magnetic field that may be detected by the biomagnetometer means, the means for simultaneously determining including an optical target adapted to be fixed to the selected portion of the human body, the optical target having a variation in optical reflectivity thereon.

2. The apparatus of claim 1, wherein the means for simultaneously determining includes
   an input optical guide that directs a beam of light at the optical target,
   a source of the beam of light provided to the input optical guide, and
   an output optical guide that collects a reflected beam of light from the optical target.

3. The apparatus of claim 2, wherein the input optical guide and the output optical guide are mounted together in an optical guide housing.

4. The apparatus of claim 1, wherein the optical target includes a central region within a background field, the central region having a different optical reflectance than the background field.

5. The apparatus of claim 1, wherein the optical target is fixed to a support surface having an adhesive backing.

6. The apparatus of claim 1, wherein the means for simultaneously determining includes position monitor means for directing a signal against the selected portion of the body and receiving a signal back from the selected portion of the body.

7. The apparatus of claim 6, wherein the means for simultaneously determining includes limit detector means for directing when the signal received back from the selected portion of the body varies outside of predetermined limits.

8. Apparatus for making magnetic measurements of a human body, comprising:

biomagnetometer means including a magnetic field sensing coil for measuring magnetic fields arising from a selected portion of the human body; a target having a variation in optical reflectivity thereon, adapted to be fixed to the selected portion of the human body; and a signal, directing the signal against the target on the and receiving a signal back from the target on the selected portion of the human body, wherein the position monitor means itself creates no magnetic field that may be detected by the biomagnetometer means, the position monitor means further including limit detector means for detecting when the signal received back from the selected portion of the human body varies outside of predetermined limits.

9. The apparatus of claim 8, wherein the target is an optical target.

10. The apparatus of claim 9, wherein the optical target includes a central region within a background field, the central region having a different reflectance than the background field.

11. The apparatus of claim 8, wherein the directed signal is a beam of energy and the position monitor means includes an input guide that directs the beam of energy at the target,
a source of the beam of energy provided to the input guide, and
an output guide that collects a reflected beam of energy from the target.

12. The apparatus of claim 11, wherein the input guide and the output guide are mounted together in an optical guide housing.

13. The apparatus of claim 8, wherein the directed signal is a beam of light and the position monitor means includes an input optical guide that directs the beam of light at the target,
a source of the beam of light provided to the input optical guide, and
an output optical guide that collects a reflected beam of light from the target.

14. The apparatus of claim 8, further including
a magnetically shielded room in which human the magnetic sensing coil is located.

15. Apparatus for making magnetic measurements of a human body, comprising:

biomagnetometer means including a magnetic field sensing coil for measuring magnetic fields arising from a selected portion of the human body; and
a position monitor comprising
an optical target adapted for placement on the selected portion of the human body, the optical target having a variation in light reflectance thereon,
an input optical guide that directs a beam of light at the target,
a source of the beam of light provided to the input optical guide,
an output optical guide that collects a reflected beam of light from the target and
limit detector means for receiving the beam of light from the output optical guide and determining whether the intensity of the received light varies outside of predetermined limits.

16. The apparatus of claim 15, wherein the limit detector means produces an electrical signal responsive to the intensity of the light received, and is located remotely from the magnetic sensing coil.

* * * * *